US00PP13289P2

(12) United States Plant Patent
Heims

(10) Patent No.: US PP13,289 P2
(45) Date of Patent: Nov. 26, 2002

(54) TIARELLA PLANT NAMED 'NEON LIGHTS'

(75) Inventor: Daniel M. Heims, Tigard, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/894,646

(22) Filed: Jun. 27, 2001

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Tiarella plant characterized by its unique leaf coloration with good vigor, fine leaf form, a clumping habit, white flowers, and profuse number of inflorescences.

2 Drawing Sheets

The present invention relates to a new and distinct hybrid of Tiarella, of the family Saxifragaceae, which originated from a cross between unknown parents. This new Tiarella was one of many seedlings grown from select plants that were mass pollinated in the greenhouse in Canby, Oreg. Due to the fact that there were several different species involved, no species designations are given.

What makes this plant unique is the high contrast between the bright green on the leaf and the dark pattern following the veins on maple shaped leaves. Tiarella 'Neon Lights' also has an outstanding number of inflorescences, excellent vigor, a clumping habit, large flowers, and an early bloom time.

The new variety has been reproduced only by asexual propagation (division and tissue culture). Each of the progeny exhibits identical characteristics to the original plant. Asexual propagation by division and tissue culture as done in Canby, Oreg., shows that the foregoing characteristics and distinctions come true to form and are established and transmitted through succeeding propagations. The present invention has not been evaluated under all possible conditions. The phenotype may vary with variations in environment without a change in the genotype of the plant.

BRIEF DESCRIPTION OF THE DRAWING

The drawing shows the new variety growing in a pot.

DETAILED PLANT DESCRIPTION

The following is a detailed description of the new Tiarella hybrid based on observations of one and a half year old specimens grown in four-gallon containers in a cool greenhouse in Canby, Oreg. The color descriptions are all based on The Royal Horticultural Society Colour Chart.

Botanical name: Tiarella hybrid.
Cultivar name: 'Neon Lights'.
Plant:
- *Form.*—Clumping, herbaceous perennial.
- *Hardiness.*—USDA Zones 4 to 9.
- *Size.*—11 cm tall and 46 cm wide; new spring leaves are upright, raising the spring height to 22 cm.

Leaf:
- *Type.*—Simple.
- *Arrangement.*—Rosette.

- *Shape.*—Broadly ovate maple leaf shape.
- *Lobing/division.*—Variable, 8–10 lobes, palmatifid, with the terminal or terminal three lobes the longest, parted almost to the vein.
- *Venation.*—Palmate, with dark coloration following veins.
- *Margins.*—Irregularly crenate, leaves often cup back slightly.
- *Apex.*—Mucronulate.
- *Base.*—Cordate, sometimes overlapping.
- *Size.*—Variable to 10 cm long and 9.5 cm wide.
- *Texture.*—Rough. Hirsute top and bottom with the bottom hairs shorter.
- *Petiole length.*—18 cm at the longest.
- *Petiole texture.*—Strongly pubescent.
- *Petiole color.*—In Spring — Greyed Orange 177A on bottom half and Yellow Green 145C on the top half. In winter between 187B and 177A.
- *Leaf color.*—The outside half of the leaf is bright green, Green 144A, with maroon pattern, Greyed Purple 187B, along the veins. In the winter it is Green 144A with Greyed Purple 187A. Abaxial side is Green 147C.

Inflorescence:
- *Type.*—Raceme.
- *Number of flowers.*—About 40 per raceme and about 90 racemes blooming in the first flush.
- *Peduncle.*—With one to two green cauline leaves, no branches. Height — 46 cm. Diameter — 0.25 cm. Color — Yellow Green 146A overall, darker at the base and tip (177A). Texture — Hispid.
- *Pedicel.*—Length — 0.8 cm. Texture — Puberulent. Color — Greyed Purple 184D.
- *Bloom period.*—April to May in Canby, Oreg.

Flower bud:
- *Size.*—0.2 cm.
- *Description.*—Puberulent, downfacing, campanulate when opening.
- *Color.*—Greyed Purple 184D.

Flower:
- *Type.*—Perfect, actinomorphic, sepals petaloid.
- *Shape.*—Rotate, with stamens extruded.
- *Size.*—Grows to 0.9 cm across and 0.6 cm deep including stamens.
- *Color.*—White 155D sepals and petals.

*Petal count.*—5.
*Petal shape.*—Elliptic with a clawed base.
*Petal size.*—0.4 cm long.
*Sepal type.*—Petaloid, divided almost to the base.
*Sepal number.*—5 lobes.
*Sepal size.*—0.35 cm.
*Stamen number.*—10, conspicuously exerted.
*Pistil color.*—White 155A.
*Pollen color.*—Orange Red 32A.
*Anther color, undehisced.*—Red Orange 31B.
*Filament color.*—White 155A.
*Fragrance.*—None.
*Lastingness.*—A raceme blooms for about 3 weeks on the plant.

Fruit:
*Type.*—A one celled, horned capsule.
*Fertility.*—Fertile.
*Color.*—Greyed-Yellow 160D.

Seed:
*Shape.*—Ovoid.
*Size.*—1.5 mm. long and 0.75 mm wide.
*Color.*—Black 202A.

Disease tolerance: Excellent disease resistance to powdery mildew, the common problem of Tiarella.

COMPARISON TO OTHER TIARELLAS

Compared to Tiarella 'Mint Chocolate' (U.S. Plant Pat. No. 11,379), Tiarella 'Neon Lights' has white flowers rather than pink, more inflorescences, and seven leaf lobes rather than five.

Compared to Tiarella 'Ninja' (U.S. Plant Pat. No. 11,168), Tiarella 'Neon Lights' has broader leaf lobes, more crenate margins, and a more distinctive leaf pattern.

Compared to Tiarella 'Spanish Cross' (U.S. Plant Pat. No. 11,345), Tiarella 'Neon Lights' has bigger leaves with rounder leaf lobes with crenate rather than jagged margins, and lighter flower buds.

Compared to Tiarella 'Jeepers Creepers' (U.S. Plant patent application Ser. No. 09/894,599), this new cultivated variety has similar leaves but a clumping, rather than creeping, habit.

I claim:

1. A new and distinct hybrid of Tiarella plant substantially as shown and described, characterized by a distinct leaf form and pattern, a clumping habit, high bud count, good vigor, and large flowers.

* * * * *

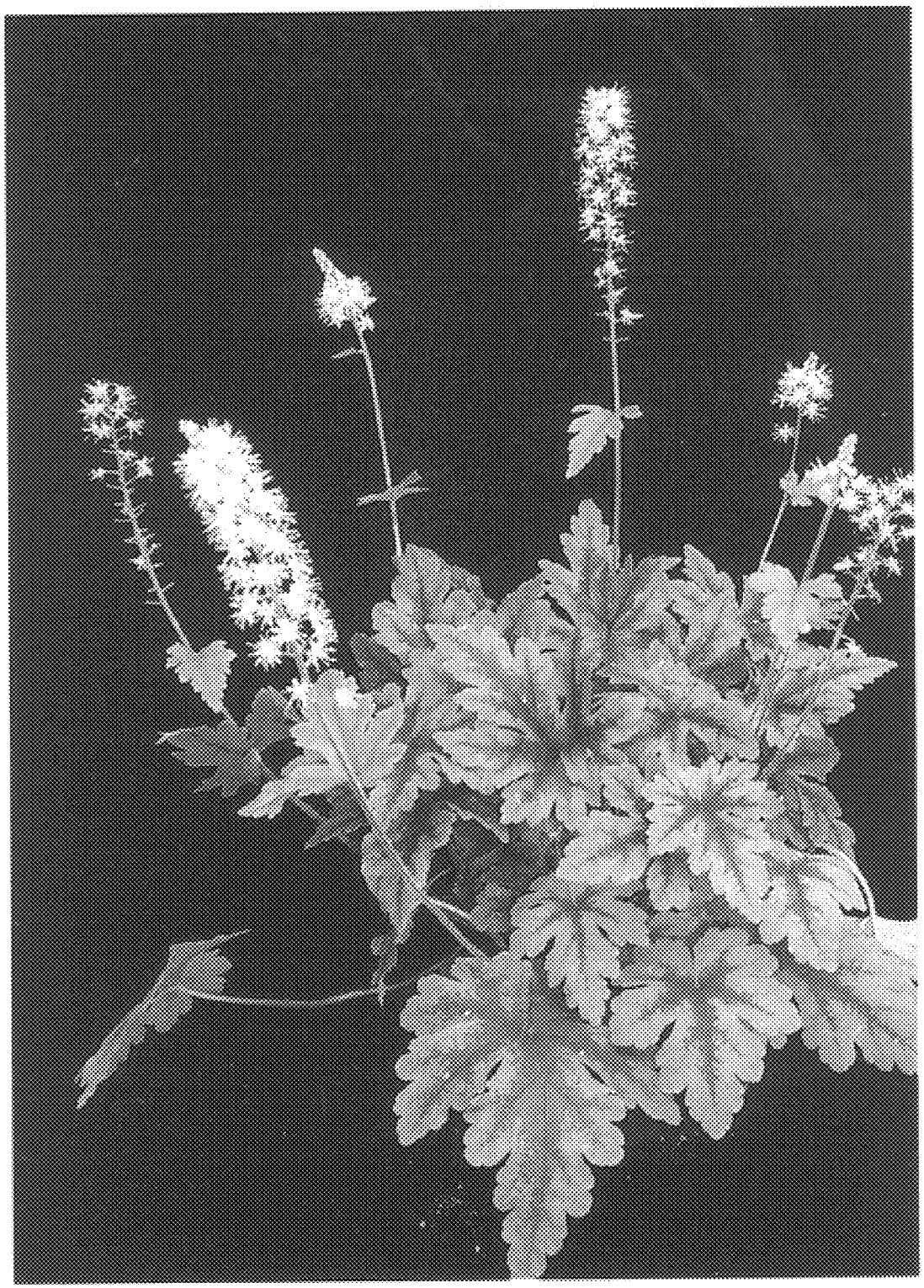

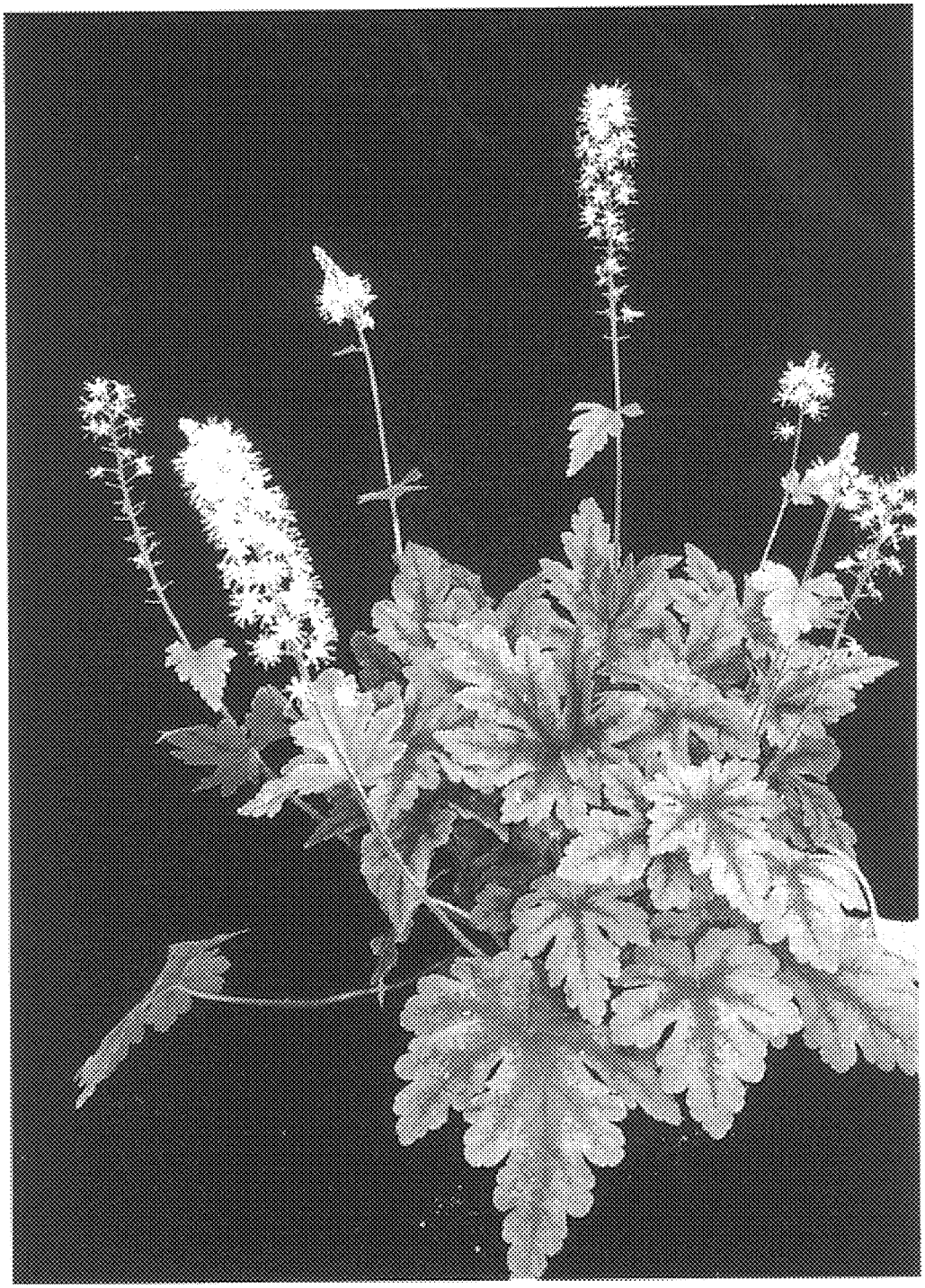

UNITED STATES PATENT AND TRADEMARK OFFICE

CERTIFICATE OF CORRECTION

PATENT NO. : PP 13,289 P2
DATED : November 26, 2002
INVENTOR(S) : Heims

It is certified that error appears in the above-identified patent and that said Letters Patent is hereby corrected as shown below:

Column 1,
Line 20, the words "possible conditions" should read -- possible environmental conditions --

Column 4,
Line 15, "09/894,599" should read -- 09/894,589 --.

Signed and Sealed this

Twenty-third Day of September, 2003

JAMES E. ROGAN
*Director of the United States Patent and Trademark Office*